United States Patent
Chan et al.

(10) Patent No.: US 8,728,017 B2
(45) Date of Patent: May 20, 2014

(54) CAPSULAR BAG REHABILITATION DEVICE

(71) Applicant: Jui-Peng Chan, Changhua (TW)

(72) Inventors: Cheng-Yang Chan, Changhua (TW); Yu-Hun Chan, Changhua (TW)

(73) Assignee: Jui-Peng Chan, Changhua (TW)

( * ) Notice: Subject to any disclaimer, the term of this patent is extended or adjusted under 35 U.S.C. 154(b) by 49 days.

(21) Appl. No.: 13/685,900

(22) Filed: Nov. 27, 2012

(65) Prior Publication Data

US 2013/0138025 A1 May 30, 2013

(30) Foreign Application Priority Data

Nov. 29, 2011 (TW) .............................. 100222488 U

(51) Int. Cl.
*A61F 5/00* (2006.01)

(52) U.S. Cl.
USPC .............................................. 602/13; 602/19

(58) Field of Classification Search
USPC ........................ 602/13, 18, 19; 128/869, 876; 2/316–318
See application file for complete search history.

(56) References Cited

U.S. PATENT DOCUMENTS

| 6,223,821 | B1 * | 5/2001 | Coronado | 166/250.01 |
| 8,529,613 | B2 * | 9/2013 | Radziunas et al. | 607/110 |
| 2005/0043660 | A1 * | 2/2005 | Stark et al. | 602/19 |
| 2007/0161933 | A1 * | 7/2007 | Ravikumar | 602/13 |
| 2012/0245491 | A1 * | 9/2012 | Amell et al. | 600/595 |

\* cited by examiner

*Primary Examiner* — Michael A. Brown
(74) *Attorney, Agent, or Firm* — Wang Law Firm, Inc.; Li K. Wang; Stephen Hsu

(57) ABSTRACT

A capsular bag rehabilitation device has a belt body with an outer layer and an inner layer and a first space and a second space formed in between. The inner layer is provided with a plurality of vent holes connecting to the ambient environment and the second space. The outer layer, the inner layer, and airbag are welded at a predetermined interval distance. The unwelded parts form network air channels in the belt body. A controller has a first air duct, a second air duct, and a pump. The controller controls the pump to pump the first space through the first air duct, or withdraw air in the first space via the first air duct and pump it into the second space via the second air duct.

9 Claims, 8 Drawing Sheets

CAPSULAR BAG REHABILITATION DEVICE

BACKGROUND OF THE INVENTION

This application claims the benefit of priority to TW 100222488, filed in the Taiwanese patent office on Nov. 29, 2011, the specification of which is incorporated in its entirety by reference.

1. Field of Invention

The invention relates to a rehabilitation device and, in particular, to a capsular bag rehabilitation device that is easy to use and does not cause discomfort due to frowziness.

2. Related Art

A conventional inflatable rehabilitation device, as shown in FIG. 8, primarily consists of a plurality of airbag 81 that are vertically stacked and can brace specific parts of the human body (such as the neck, waist, etc.). An inflating handball 82 is used to connect to the airbags 81, so that the airbags 81 can be inflated by the inflating handball 82 to have a brace action. This can stretch the neck or waist to achieve the effect of rehabilitation.

However, the above mentioned inflatable rehabilitation device relies on manual inflation in practice. Therefore, it is very laborious and inconvenient. Moreover, the airbags 81 have to brace the human neck for a long time. The user may feel frowziness and discomfort of the neck.

SUMMARY OF THE INVENTION

An objective of the invention is to provide a bag rehabilitation device that is easy to use and does not cause discomfort due to frowziness.

To achieve the above mentioned objective, the invention provides a capsular bag rehabilitation apparatus comprising a belt body and a controller.

The belt body has an outer layer and an inner layer. Between the outer layer and the inner layer, that is formed with a first space facing the outer layer and a second space facing the inner layer. The inner layer is formed with a plurality of vent holes connecting to the ambient environment as well as the second space. The outer layer, the inner layer, and the airbag are welded in accordance with a predetermined interval distance. The unwelded parts form network air channels in the belt body.

The controller has a first air duct and a second air duct. The first air duct is connected with the first space of the air bag, and the second air duct is connected with the second space of the airbag. The controller is equipped with a pump connected with the first air duct and the second air duct. The controller controls the pump to inflate the first space via the first air duct, or to withdraw air from the first space via the first air duct to inflate the second space via the second air duct.

When the pump inflates the first space, the injected air expands the belt body. When the pump extracts the air from the first space then inflates the second space via the second air duct, the air injected into the second space is released via the vent holes, removing the expanding state of the belt body.

BRIEF DESCRIPTION OF THE DRAWINGS

These and other features, aspects and advantages of the invention will become apparent by reference to the following description and accompanying drawings which are given by way of illustration only, and thus are not limitative of the invention, and wherein.

DETAILED DESCRIPTION OF THE INVENTION

The present invention will be apparent from the following detailed description, which proceeds with reference to the accompanying drawings, wherein the same references relate to the same elements.

Figure 1:
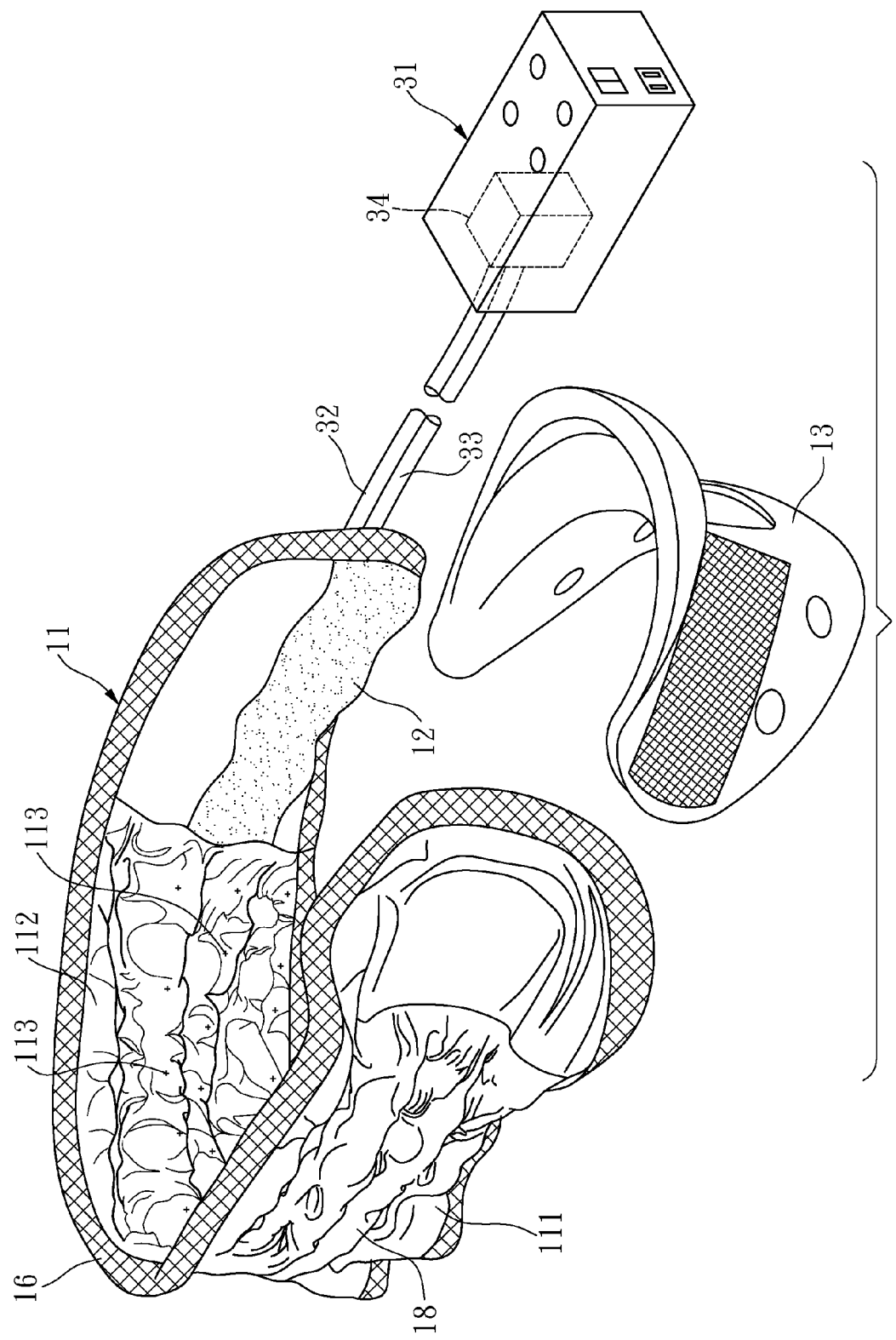
FIG. 1 is a three-dimensional perspective view of the invention.
Figure 2:
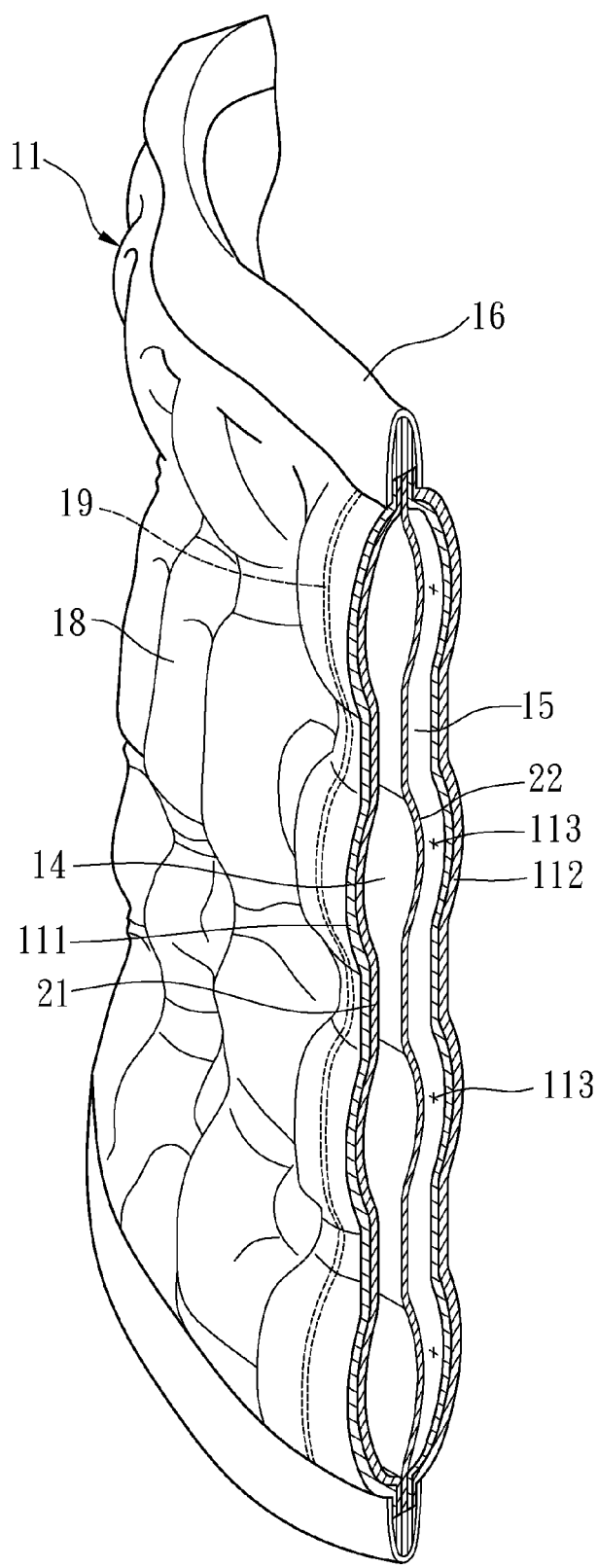
FIG. 2 is a schematic structural view of the invention.

First, please refer to FIGS. 1 and 2 for a capsular bag rehabilitation device of the invention. It mainly consists of a belt body 11 and a controller 31.

The belt body 11 extends toward a predetermined direction like a belt. Both ends of the belt body 11 have a sticky fastener 12, respectively. The sticky fasteners 12 of the belt body 11 allow the adhesion of an arc-shaped lower jaw protector 13. The combination of the belt body 11 and the lower jaw protector 13 can then be braced around the neck of a human body. The belt body 11 has an outer layer 111 facing outward and an inner layer 112 for contact with the human body. Between the outer layer 111 and the inner layer 112 is formed with a first space 14 facing the outer layer 111 and a second space 15 facing the inner layer 112. The first space 14 and the second space 15 are not in fluid communication. In this embodiment, the outer layer 111 and the inner layer 112 sandwiches an air bag 21. A barrier 22 is provided in the interior of the airbag 21, so that the air bag 21 is internally divided into the first space 14 and the second space 15. The inner layer 112 is formed with a plurality of vent holes 113 connecting to the ambient environment and the second space 15.

The outer surface 111, the inner layer 112 and the surrounding of the airbag 21 are fixed by sewing with a side tape 16, thereby forming the belt body 11. The belt body 11 is treated with high frequency welding at a predetermined interval distance, fusing the outer layer 111, the inner layer 112, and the airbag 21 at the welding places. The unwelded parts form network air channels 18 inside the belt body 11. The interior of the belt body 11 is provided with a plurality of long strips-shaped elastic elements 19. One end of each of the elastic elements 19 is attached to the upper edge of the side tape 16. The other end thereof is connected to the lower edge of the side tape 16. The belt body 11 can be pulled by the elastic elements 19. This enables the outer layer 111, the inner layer 112, and the airbag 21 of the belt body 11 to retract. The belt body 11 is then tightened on both upper and lower portions.

The controller 31 has a first air duct 32 and a second air duct 33. The first air duct 32 is in fluid communications with the first space 14 of the airbag 21. The second air duct 33 is in fluid communications with the second space 15 of the airbag 21. The controller 31 is provided with a pump 34 connecting to the first air duct 32 and the second air duct 33. The controller 31 controls the pump 34 to inflate the first space 14 of the airbag 21 via the first air duct 32. Or, it extracts air from the first space 14 of the airbag 21 via the first air duct 32 to inflate the second space 15 via the second air duct 33.

Figure 3:
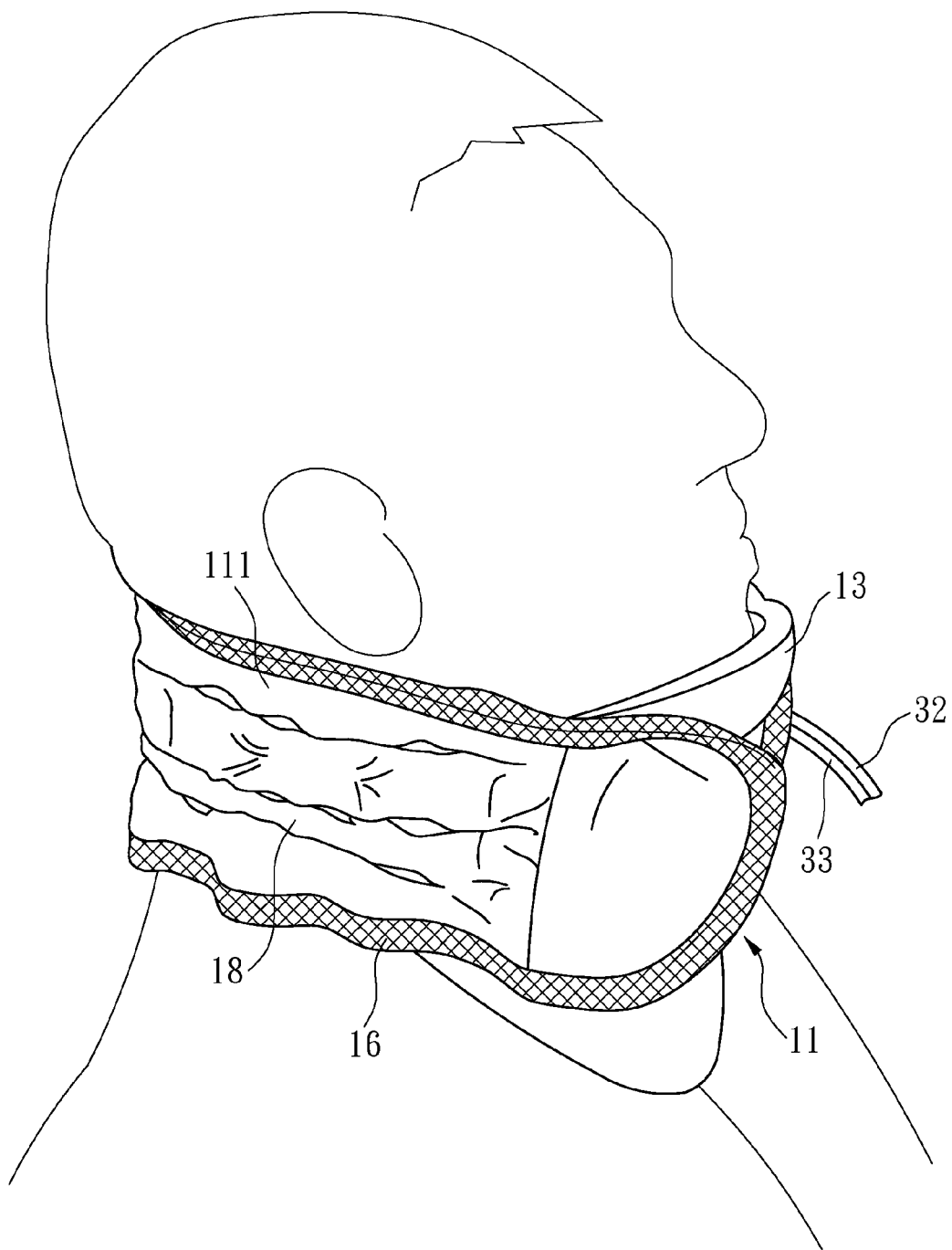
FIG. 3 is a schematic view showing the invention in use, particularly the state when both the upper and lower parts of the belt body are contracted.

When the pump 34 is not pumping, as shown in FIGS. 1 and 3, the disclosed capsular bag rehabilitation device uses the pulling forces provided by the elastic elements 19 to tighten the upper and the lower portions of the belt body 11.

Figure 4:
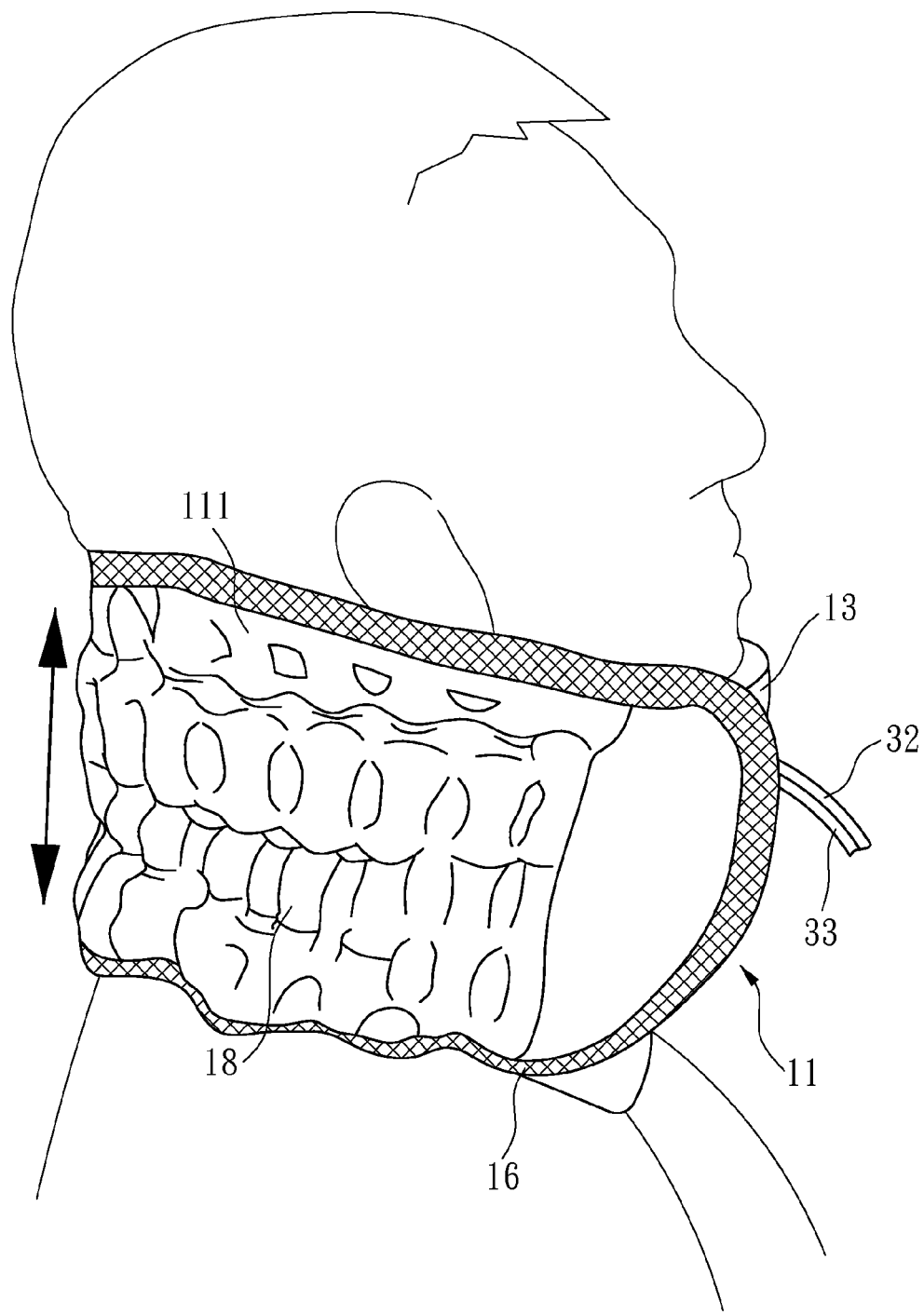
FIG. 4 is a schematic view showing the invention in use, particularly the expanding state when the belt body expands upward and downward.
Figure 5:
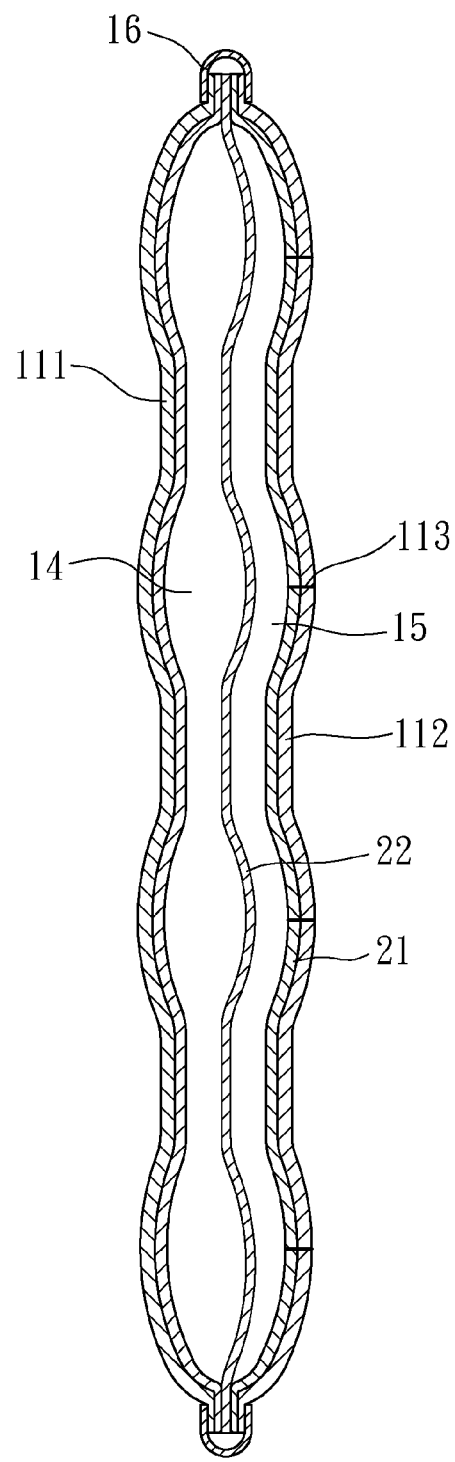
FIG. 5 is a schematic view showing the invention in use, particularly when the pump inflates the first space.

When the inner layer 112 of the belt body 11 braces around a human neck and the controller 31 controls the pump 34 to inflate the first space 14 via the first air duct 32, as shown in FIGS. 4 and 5, air is continuously pumped into the first space 14, so that the first space 14 becomes gradually inflated. This pulls the elastic elements 19 and stretches the belt body 11 upward and downward, reaching an expanding state. This stretches the neck.

Figure 6:
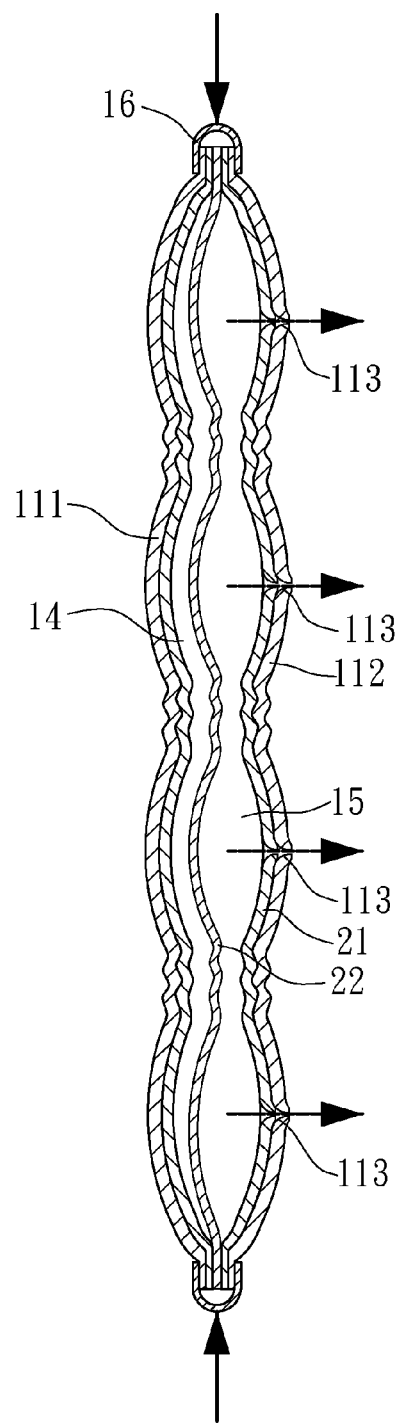
FIG. 6 is a schematic view showing the invention in use, particularly when the pump extracts the air in the first space to inflate the second space.

After the pump 34 inflates the first space 14, the controller 31 controls the pump to extract the air inside the first space 14 via the first air duct 32 after is fastened to a predetermined delay time. It then pumps the air into the second space 15 via the second air duct 33. As shown in FIG. 6, the air inside the second space 15 is gradually released via the vent holes 113, thereby releasing the belt body 11 from the expanding state, as shown in FIG. 3. When the belt body 11 is pulled by the elastic elements 19, it simultaneously squeezes the second space 15 so that the air is fully pushed out via the vent holes 113. Since the vent holes 113 are provided on the inner layer 112 in contact with the human neck, the air leaving the second space 15 via the vent holes 113 further generates a blowing effect directly on the human neck. This can effectively avoid the frowziness and discomfort of the neck.

The controller 31 can control the pump 34 to constantly perform a reciprocal motion to expand the belt body 11. This imposes a reciprocal stretching motion on the human neck, thereby achieving the effect of neck rehabilitation. In practice, the invention can set different delay times and other settings of the controller 31 in accordance with the users' needs. Since the circuit configuration belongs the prior art, it is not further described herein.

Figure 7:
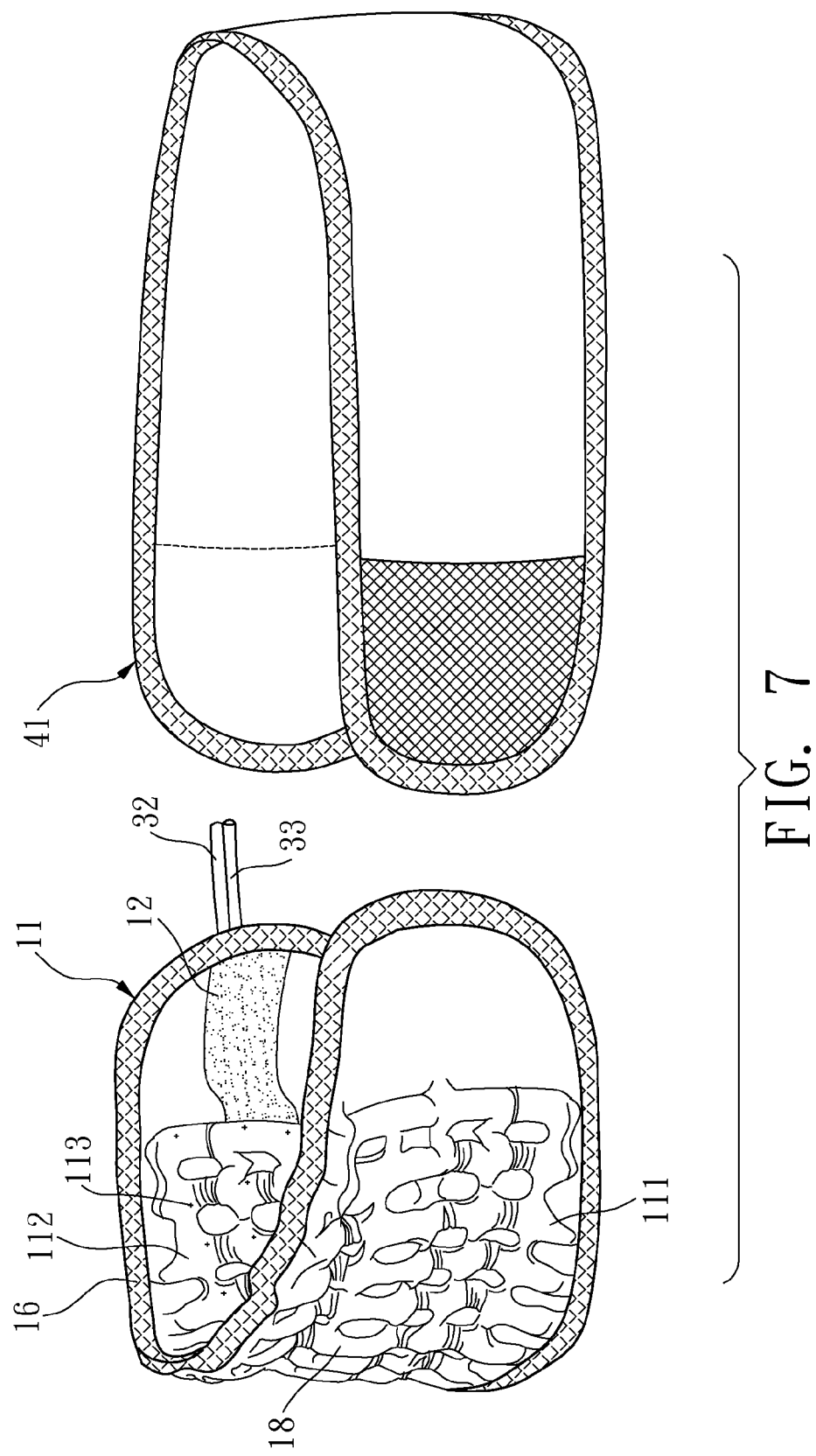
FIG. 7 is a three-dimensional perspective view of a second embodiment of the invention.
Figure 8:
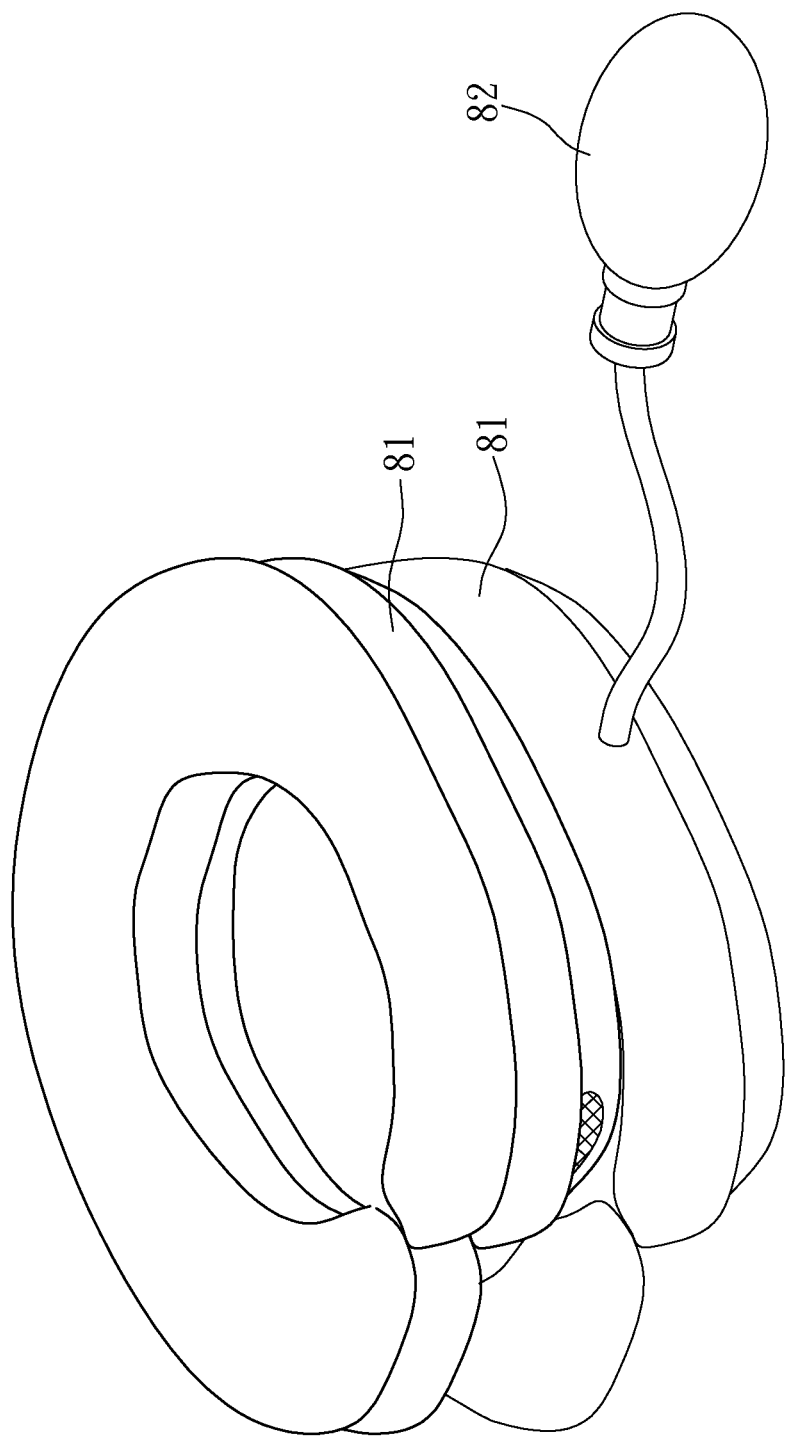
FIG. 8 is a three-dimensional perspective view of a conventional inflatable rehabilitation device.

FIG. 7 shows another embodiment of the invention. It differs from with the above-described embodiment in that the sticky fasteners 12 on both ends of the belt body 11 can be adhered with a band 41. The combination of the belt body 11 and the band 41 can be used to brace a human waist to stretch the waist spine reciprocally, achieving the effect rehabilitating the waist spine.

The invention has the following advantages:

1. The disclosed capsular bag rehabilitation device uses the controller to achieve the effects of automatic inflation and deflation. Thus, it is easy to use.

2. The disclosed capsular bag rehabilitation device uses the controller to control the pump, which then drives the belt body to perform a reciprocal stretching action. This achieves the effects of rehabilitating neck/waist spines.

3. When the disclosed capsular bag rehabilitation device releases the expanding state of the belt body, the vent holes produce a blowing effect to the part of human body on which the invention is used. This can effectively eliminate frowziness and discomfort of that part of human body.

Although the invention has been described with reference to specific embodiments, this description is not meant to be construed in a limiting sense. Various modifications of the disclosed embodiments, as well as alternative embodiments, will be apparent to people skilled in the art. Therefore, it is contemplated that the appended claims will cover all modifications that fall within the true scope of the invention.

What is claimed is:

1. A capsular bag rehabilitation device, comprising:
a belt body having an outer layer and an inner layer, between which are formed with a first space facing the outer layer and a second space facing the inner layer, the inner layer being formed with a plurality of vent holes connecting to the ambient environment and the second space, the outer layer and the inner layer being welded at a predetermined interval distance, and unwelded parts forming a network of air channels inside the belt body; and
a controller having a first air duct in fluid communications with the first space, a second air duct being in fluid communications with the second space, and a pump in fluid communications with the first and second air ducts, the controller controlling the pump to inflate the first space via the first air duct or extracts the air in the first space via the first air duct to inflate the second space via the second air duct;
wherein as the pump inflates the first space, the belt body is stretched by the injected air; and when the pump extracts the air in the first space and inflates the second space via the second air duct, the air injected into the second space leaves via the vent holes, thereby releasing the belt body from the stretching state.

2. The capsular bag rehabilitation device of claim 1, wherein the belt body extends toward a predetermined direction into a long strip, and both ends thereof have a sticky fastener, respectively.

3. The capsular bag rehabilitation device of claim 2, wherein the sticky fasteners of the belt body is provided for the adhesion of a lower jaw protector, so that the combination of the belt body and the lower jaw protector is to brace a human neck.

4. The capsular bag rehabilitation device of claim 2, wherein the sticky fasteners on both ends of the belt body are provided for the adhesion of a band, so that the combination of the belt body and the band is to brace around a human waist.

5. The capsular bag rehabilitation device of claim 1, wherein an airbag is sandwiched between the outer layer and the inner layer, the capsular bag is further provided with a barrier to divide the interior thereof into the first space and the second space.

6. The capsular bag rehabilitation device of claim 5, wherein the outer layer, the inner layer, and the surrounding of the airbag are fixed by sewing with a side band to form the belt body.

7. The capsular bag rehabilitation device of claim 6, wherein the interior of the belt body has a plurality of long strip-shaped elastic elements, each of which is connected to the upper edge of the side band on one end and connected to the lower edge of the side band on the other end, so that the belt body is pulled by the elastic elements to contract the outer layer, the inner layer, and the airbag of the belt body, thereby contracting the upper and lower portions of the belt body when the belt body is not inflated.

8. The capsular bag rehabilitation device of claim 5, wherein the belt body is treated with high-frequency welding at a predetermined interval distance, so that the outer layer, the inner layer, and the airbag are connected.

9. The capsular bag rehabilitation device of claim 1, wherein after the pump inflates the first space, the controller controls the pump to extract the air inside the first space to inflate the second space via the second air duct after a predetermined delay time.

* * * * *